US005606023A

United States Patent [19]

Chen et al.

[11] Patent Number: 5,606,023

[45] Date of Patent: Feb. 25, 1997

[54] MUTANT TUMOR NECROSIS FACTOR PROTEINS

[75] Inventors: Mann-Jy Chen, Wayne; Irene T. Weber, Haverford, both of Pa.

[73] Assignee: Thomas Jefferson University, Philadelphia, Pa.

[21] Appl. No.: 249,190

[22] Filed: May 24, 1994

[51] Int. Cl.$^6$ ........................ C07K 14/525; A61K 38/19; C12N 15/28

[52] U.S. Cl. ........................ 530/351; 424/85.2; 435/69.52

[58] Field of Search ........................ 435/69.52; 424/85.1, 424/85.2; 514/2, 8, 12; 530/350, 351

[56] References Cited

FOREIGN PATENT DOCUMENTS 0810224 3/1993 Canada .

OTHER PUBLICATIONS

Gennaro, Alfonso, Ed., *Remington's Pharmaceutical Sciences*, 18th Edition, Mack Publishing Co., Easton, PA, 1990.

Goodwin et al., "Molecular cloning and expression of the type 1 and type 2 murine receptors for tumor necrosis factor", *Mol. Cell Biol.* 1991, 11:3020–3026.

Gray et al., "Cloning of human tumor necrosis factor (TNF) receptor cDNA and expression of recombinant soluble TNF––binding protein", *Proc. Natl. Acad. Sci. USA* 1990, 87:7380–7384.

Kunkel T. A., "Rapid and efficient site–specific mutagenesis without phenotypic selection", *Proc. Nat'l. Sci. USA* 1985 82:488–492.

Kunkel T. A. et al., "Rapid and efficient site–specific mutagenesis without phenotypic selection", *Methods in Enzymol.*, 154:367–382.

Loetscher et al., "Molecular cloning and expression of the human 55 kd tumor necrosis factor receptor", *Cell* 1990, 61:351–359.

Loetscher et al., "Human Tumor Necrosis Factor α(TNFα) Mutants with Exclusive Specificity for the 55–kDA or 75–kDA TNF Receptors", *J. Biol. Chem.*, 1993, 268(35):26350–26358.

Schall et al., "Molecular cloning and expression of a receptor for tumor necrosis factor", *Cell* 1990, 61:361–370.

Shortle D. et al., "Local mutagenesis: A method for generating viral mutants with base substitutions in preselected regions of the viral genome", *Proc. Nat'l, Sci. USA* 1978, 75:2170–2174.

Smith et al., "A receptor for tumor necrosis factor defines an unusual family of cellular and viral proteins", *Science* 1990, 248:1019–1023.

Van Ostade et al., "Human TNF mutants with selective activity on the p55 receptor", *Nature* 1993, 361:266–268.

Zhang et al., "Site–directed Mutational Analysis of Human Tumor Necrosis Factor–α Receptor Binding Site and Structure–Functional Relationship", *J. Biol. Chem.* 1992, 267(33):24069–24075.

Schulz & Schirmer, published 1979, by Springer–Verlag New York, Inc., pp. 14–16.

Barbara et al. (1994), The EMBO Journal, vol. 13, pp. 843–850.

Varr Ostade et al. (1994) Eur. J. Biochem, vol. 220, pp. 771–779.

Bouie et al. (1990), Science vol. 247 pp. 1306–1310.

*Primary Examiner*—John Ulm
*Assistant Examiner*—Prema Mertz
*Attorney, Agent, or Firm*—Law Offices of Jane Massey Licata

[57] ABSTRACT

Mutant tumor necrosis factor proteins which retain full or near full capability to bind to a TNFR-p75 receptor while retaining only a limited capability to bind a TNFR-p55 receptor are provided. Methods of inhibiting toxicity induced by tumor necrosis factor by treating cells or tissues having a tumor necrosis factor receptor with these mutant human tumor necrosis factor proteins are also provided. Pharmaceutical compositions and methods of inhibiting systemic tumor necrosis factor induced toxicity in a patient undergoing antitumor TNF-α therapy with these compositions are also provided.

2 Claims, 1 Drawing Sheet

MUTANT TUMOR NECROSIS FACTOR PROTEINS

INTRODUCTION

This invention was made with government support under a grant from the National Institutes of Health. The U.S. Government may have certain rights in this invention.

BACKGROUND OF THE INVENTION

Tumor necrosis factor α (TNFα) is a cytokine primarily produced by activated macrophages. TNFα stimulates T-cell and B-cell proliferation and induces expression of adhesion molecules on endothelial cells. This cytokine also plays an important role in host defense to infection.

TNFα activities are mediated through two distinct receptors, TNFR-p55 and TNFR-p75. These two receptors also mediate activities triggered by soluble lymphotoxin α (LT-α) secreted mainly by activated lymphocytes. Specific stimulation of TNFR-p55 induces TNF activities such as in vitro tumor cell cytotoxicity, expression of adhesion molecules on endothelial cells and keratinocytes, activation of sphingomyelinase with concomitant increases of ceramide, activation of NF-κB and induction of manganese superoxide dismutase mRNA. Specific stimulation of TNFR-p75 results in proliferative response of mouse and human thymocytes and cytoxic T cells, fibroblasts and natural killer cells and in GM-CSF secretion in PC60 cells.

TNF, especially in combination with γ-interferon (IFN-γ), has the ability to selectively kill or inhibit malignant cell lines that is unmatched by any other combination of cytokines. Clinical trials in cancer patients with TNF-α antitumor therapy have been disappointing, however, because the toxic side effects of TNF have prevented obtaining effective dose levels in man. These toxic side effects have been attributed to TNF binding to the TNFR-p75 receptor while the cytotoxic activity on malignant cells has been attributed to binding of TNF to the TNFR-p55 receptor.

TNFR-p55 and TNFR-p75 from human (Loetscher et al., "Molecular cloning and expression of the human 55 kd tumor necrosis factor receptor", *Cell* 61:351–359, 1990; Gray et al., "Cloning of human tumor necrosis factor (TNF) receptor cDNA and expression of recombinant soluble TNF-binding protein", *Proc. Natl. Acad. Sci. USA* 87:7380–7384, 1990; Schall et al., "Molecular cloning and expression of a receptor for tumor necrosis factor", *Cell* 61:361–370, 1990; Smith et al., "A receptor for tumor necrosis factor defines an unusual family of cellular and viral proteins", *Science* 248:1019–1023, 1990) and mouse (Goodwin et al., "Molecular cloning and expression of the type 1 and type 2 murine receptors for tumor necrosis factor", *Mol. Cell Biol.* 11:3020–3026, 1991); have been cloned. Random and site-specific mutagenesis have shown that amino acids involved in receptor binding of TNF are located at each interface between two subunits, particularly loops 29–36, 84–91, and 143–148. Loetscher et al., "Human Tumor Necrosis Factor α(TNFα) Mutants with Exclusive Specificity for the 55-kDA or 75-kDa TNF Receptors", *J. Biol. Chem.*, 268(35):26350–26358, (1993) reported that generally, mutations in the loop from position 29 to 34 and at positions 86 and 146 preferentially impaired binding to the 75-kDa TNF receptor, while mutations in the region from 143 to 145 mainly affected binding to the 55-kDa TNF receptor.

Two TNF mutants, L29S and R32W, which have been characterized in detail, have maintained almost completely the ability to bind TNFR-p55, while the TNFR-p75 affinity is decreased drastically (Van Ostade et al., "Human TNF mutants with selective activity on the p55 receptor", *Nature* 361:266–268, 1993). Van Ostade et al. also found that charge reversal at position 146 (E146K) resulted in a marked differential binding and activity. The R32W and E146K mutants were also shown to have decreased activity toward neutrophils and endothelial cells, two cells type believed to play an important rule in TNF-induced systemic toxicity. Thus, it was suggested that the use of TNF-R55-specific mutants, L29S, R32W and E146K in cancer patients may result in reduced general toxicity. A reversed differential binding affinity for TNFR-p75 was less affected as compared to TNFR-p55, and concomitant receptor-mediated activity has also been observed with several substitutions at position 143 in human TNF.

Zhang et al., "Site-directed Mutational Analysis of Human Tumor Necrosis Factor-α Receptor Binding Site and Structure-Functional Relationship" *J. Biol. Chem.* 267(33):24069–24075 (1992) examined the structure and functional relationship of site-directed mutation of TNF on receptor binding and found the loop containing $Tyr^{87}$ of the TNF molecule to be the most likely to make direct contact with the TNF receptor. It is suggested that since $Tyr^{87}$ may form a hydrogen bond with $Ala^{33}$, proline substitution at nearby residues on the same loop as $Ala^{33}$ could impair the normal interaction of $Ala^{33}$ with $Tyr^{87}$ by altering the backbone conformation, leading to impaired receptor binding. The effect of mutation at the $Ala^{33}$ position was not examined in these experiments.

It has now been found that conservative mutations of the alanine at position 33 does not impair receptor binding to TNFR-p75, but rather results in mutant human tumor necrosis factor-α proteins which retain full or near full capability to bind to the TNFR-p75 receptor while retaining only a limited capability to bind the TNFR-p55 receptor. These mutant tumor necrosis factor proteins, if acting as TNFR-p75 antagonists, are useful in inhibiting systemic toxicity induced by TNF. On the other hand, if these mutant TNF-α proteins act as TNFR-p75 agonists, they are useful as TNFR-p75 specific desensitizers at lower doses which suppress systemic toxicity. These mutant proteins are useful as immune stimulators due to their ability to promote lymphocyte proliferation.

SUMMARY OF THE INVENTION

An object of the invention is to provide mutant tumor necrosis factors proteins which retain full or near full capability to bind to a TNFR-p75 receptor while retaining only a limited capability to bind a TNFR-p55 receptor.

Another object of the invention is to provide a method of inhibiting toxicity of tumor necrosis factor which comprises treating a cell or tissue having a tumor necrosis factor receptor with an effective amount of a mutant human tumor necrosis factor protein which is capable of retaining full or near full capability to bind to a TNFR-p75 receptor while retaining only a limited capability to bind a TNFR-p55 receptor so that toxicity is inhibited.

Yet another object of the invention is to provide a method of inhibiting systemic TNF-α induced toxicity in a patient suffering from a tumor and undergoing TNF-α therapy which comprises administering to the patient an effective amount of a pharmaceutical composition, the pharmaceutical composition comprising a mutant human tumor necrosis factor protein which is capable of retaining full or near full capability to bind to a TNFR-p75 receptor while retaining only a limited capability to bind a TNFR-p55 receptor and a pharmaceutically acceptable carrier, so that the systemic toxicity associated with TNF-α antitumor therapy is inhibited.

BRIEF DESCRIPTION OF THE FIGURES

In FIG. 1(A) the binding affinities of A33-Ile and wild type TNF for the TNFR-p55 receptor are compared. In FIG. 1(B) the binding affinities of A33-Ile and wild-type TNF for the TNFR-p75 receptor are compared.

DETAILED DESCRIPTION OF THE INVENTION

Figure 1A:
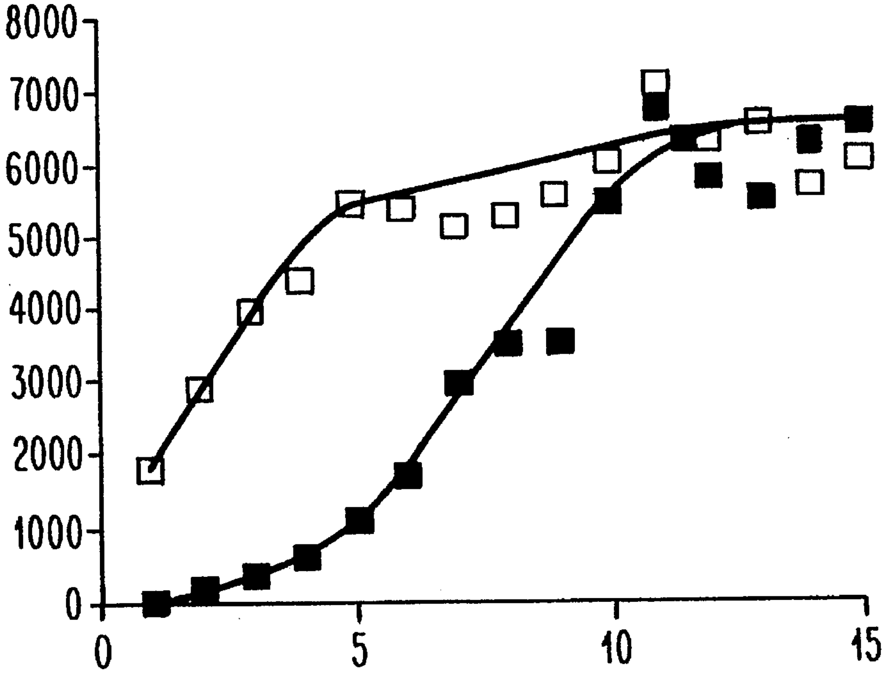
FIGS. 1(A) and 1(B) are graphs of data obtained in a solid phase receptor binding inhibition assay with the mutant TNF protein A33-Ile (□) and wild type TNF (■) wherein the x axis represents the number of 2 fold serial dilutions of the TNF proteins and y axis represents counts per minute bound to the receptor.

The biological activities of tumor necrosis factor (TNF-α) vary greatly, ranging from beneficial activities such as tumor cell killing to detrimental activities such as fever, septic shock and cachexia. The in vivo systemic toxicity of TNF has been attributed to TNF binding to the TNFR-p75 receptor while the beneficial tumor killing activity has been attributed to binding of TNF to the TNFR-p55 receptor on tumor vasculature endothelial cells and neutrophils in addition to its binding to the TNFR-p55 receptor on malignant cells in the tumor. In the present invention, mutant tumor necrosis factor proteins which retain full or near full capability to bind to a TNFR-p75 receptor while retaining only a limited capability to bind to a TNFR-p55 receptor are provided. These proteins are useful in inhibiting the systemic side effects associated with administration of TNF.

By the term "mutant tumor necrosis factor" it is meant a human tumor necrosis factor-α (TNF-α) protein which has one or more amino acid substitutions in the protein sequence. In a preferred embodiment, these mutated proteins possess none or very little of the biological activities associated with the TNF protein. In the present invention the amino acid substitutions render the mutated proteins with a full or near full capability as compared to TNF-α to bind to the TNFR-p75 receptor while retaining only a limited capability as compared to TNF-α to bind to the TNFR-p55 receptor. A protein of the invention which retains full or near full capability to bind to a TNFR-p75 receptor while retaining only a limited capability to bind a TNFR-p55 receptor has a ratio of the affinity of the protein to bind to the TNFR-p75 receptor over its affinity toward the TNFR-p55 receptor which is greater than 5. Wild type TNF has a binding affinity to TNFR-p75 which is approximately 5 fold higher than its binding affinity to TNFR-p55. Therefore, at low concentrations, wild type TNF binds to TNFR-p75 before binding to TNFR-p55 occurs. Mutant TNF proteins of the present invention have a larger window of ligand concentration within which binding to TNFR-p75 but not binding to TNFR-p55 occurs. In a preferred embodiment, at least one substitution is made to the alanine at position 33 of the TNF-α protein sequence. Substitutions of the alanine at position 33 with isoleucine, leucine, asparagine or valine are most preferred. Though various mutations of TNF-α have been described in the art, product or composition of matter with full or near full capability to bind TNFR-p75 while maintaining only a limited capability to bind TNFR-p55 having a mutation at the 33 position have not been described prior to this disclosure.

TNF mutants, with amino acid substitutions in at least one position, are created by site-directed mutagenesis. Site-directed mutation can be performed in accordance with several procedures well known to those of skill in the art. See, Shortle D. et al., *Proc. Nat'l, Sci. USA* 1978 75:2170–2174; Kunkel T. A., *Proc. Nat'l. Sci. USA* 1985 82:488–492; Kunkel T. A. et al. , *Methods in Enzymol.*, 154:367–382. In a preferred embodiment a phagemid mutagenesis/expression vector is constructed. An example of such a vector is PUC118hTNF. Other similar vectors which can also be used can be constructed by inserting human TNF-α mature protein coding sequence into pTZ vectors (Bio-Rad, Hercules, Calif.).

The properties of the mutants are tested with bacterial crude lysate containing recombinant mutants. Mutant properties analyzed include protein yield, solubility, trimer formation, in vitro cytotoxic activity and receptor binding inhibition activity. It has been observed that mutants which do not form a cross-linkable trimer also show little cytotoxic activity or receptor binding inhibition activity.

The effect of a mutation to the TNF-α protein on the binding of the mutated protein to each of the individual TNF receptors is tested in receptor binding assays performed in cell lines expressing only one of the two TNF receptors. Examples of such cell lines include, but are not limited to, MCF-7 human breast carcinoma cell line or Hep 2 human larynx epidermoid carcinoma cell line which express only the TNFR-p55 receptor and Raji human Burkitt lymphoma cell line which expresses only the TNFR-p75 receptors. In binding studies wherein the TNF-α protein was mutated at position 33, it was found that substitution of the alanine to asparagine, isoleucine, valine, or leucine decreased the affinity of the protein to TNFR-p55 but did not significantly change the affinity of the protein to TNFR-p75.

The receptor discriminating mutants of the present invention are useful as TNFR-p75 specific agonists or antagonists. The high specificity of binding to the TNFR-p75 receptor makes the mutant proteins of the present invention effective without the need for administration of excessively high doses. Such mutants can be used as antiinflammatory agents, as antitumor cotherapeutic agents to reduce systemic toxicity induced by TNF-α or as positive immunoregulators in vivo.

In one embodiment the mutant proteins of the present invention can be used to inhibit systemic toxicity induced by tumor necrosis factor. Cells or tissue having a tumor necrosis factor receptor can be treated with an effective amount of a mutant human tumor necrosis factor protein which is capable of retaining full or near full capability to bind to a TNFR-p75 receptor while retaining only a limited capability to bind a TNFR-p55 receptor resulting in inhibition of the toxicity associated with tumor necrosis factor. An "effective amount" refers to a concentration, which can be routinely determined by one of skill in the art in accordance with the teachings of the present invention, of a mutant human tumor necrosis factor protein which is capable of inhibiting systemic toxicity associated with tumor necrosis factor. By "inhibiting" it is meant that the toxic side effects attributed to TNF binding to the TNFR-p75 receptor are lessened when cells or tissues having a TNF receptor are treated with a mutant human tumor necrosis factor protein in the presence of TNF. By "TNF receptor" it is meant to include both the TNFR-p55 and the TNFR-p75 receptors.

The mutant proteins of the present invention can also be administered to patient as antitumor cotherapeutic agents to reduce systemic toxicity induced by TNF-α. An effective amount of a pharmaceutical composition comprising a mutant protein of the present invention and an acceptable pharmaceutical carrier can be administered to patient suffering from a tumor and undergoing TNF-α therapy to reduce the systemic toxicity associated with TNF-α antitumor therapy. Suitable pharmaceutically acceptable carriers which can be used in the present invention are well known in the art and are described for example in Gennaro, Alfonso, Ed., *Remington's Pharmaceutical Sciences,* 18th Edition 1990. Mack Publishing Co., Easton, Pa., a standard reference text in this field. Pharmaceutical carriers may be selected in accordance with the intended route of administration and the standard pharmaceutical practice. Persons of ordinary skill can easily determine optimum dosages, dosing methodologies and repetition rates in accordance with the weight and condition of the patient.

The mutant proteins of the present invention also provide a means for studying the specific signal transduction pathways of the TNFR-p75 receptor and to depict the pathophysiological or the physiological conditions mediated specifically by this receptor. By such studies the development of therapeutic and prophylactic agents which can modulate these conditions is facilitated.

The invention is further illustrated by the following nonlimiting examples.

EXAMPLES

Example 1

Construction of Phagemid Mutagenesis/Expression Vector

The construction of phagemid mutagenesis/expression vector PUC118htnfwt was performed by a two-step polymerase chain reaction (PCR) synthesis procedure using standard conditions with a PCR kit (Perkin Elmer Cetus, Norwalk, Conn.). For the first step in the PCR synthesis, a pair of primers with sequences:

5' CTAAGGAAAT ACTTACATAT GGTACGTTCT TCTTCTCGTA CTCCGAGTGA
CAAGCCTGT 3' (primer 1; SEQ ID NO: 1)
5' TTAAAGTTCT AAGCTTGGGT 3' (primer 2; SEQ ID NO: 2)

were used with a plasmid DNA derived from the human TNF cDNA clone pHGE or pE4 as the DNA template. Primer 1 recreates, following an added ATG start codon (indicated in bold), the first seven amino acids of the mature TNF coding sequence in *E. coli* preferred codons, followed by 17 bases complementary to the 8th through the second base of the 13th codons. Primer 2 contains a sequence matching the human TNF cDNA sequence downstream of the termination codon around the unique Hind III site. A 633 base pair product was synthesized in this first step. The identity of the product was verified by agarose gel electrophoresis. The primers were removed with a size selection filter and the first step PCR product was then used as a template for the second step of the PCR synthesis. Primer 3 with the following sequence:

5' TCGACATGCA TTTATTTGCA TACATTCAAT CAATTGT-
TAT CTAAGGAAAT
ACTTACATAT G 3' (primer 3; SEQ ID NO:3)

and primer 2 shown above were used in the second PCR step. Primer 3 contains a Nsi I site and 21 bases which are homologous with the first step PCR product. Following the second step PCR synthesis, the primers were removed by size selection filters. The 673 base pair product was cut with Nsi/Hind III restriction enzymes, ligated to Pst I/Hind III restricted PUC118 DNA, and transformed into *E. coli* strains CJ236 and MV1190. Mutagenesis was performed using a Bio-rad (Hercules, Calif.) phagemid mutagenesis kit in accordance with the manufacturer's direction with the exception the a VCSM13 helper phage purchased from Stratagene (La Jolla, Calif.) was used instead of M13K07.

Example 2

Preparation of Bacterial Crude Lysates

For expression, culture of PUC118hTNF transformed MV1190 or 1193 was grown overnight, and bacterial crude lysates containing recombinant proteins were prepared as follows. Bacteria harboring the wild type or mutant TNF expressing phagemids were grown at 37° C. overnight in LB media with antibiotics, pelleted by centrifugation, resuspended in 1/10 volume of 10 mM Tris HCl, pH 7.5 and sonicated in a 1.5 ml microfuge tube until complete lysis occurs. The lysates were then clarified by centrifugation at 13 kRPM in a microfuge for 5 min at 4° C. The supernatant derived from centrifugation is the crude extract. The pellet fraction is resuspended in the same volume of 10 mM Tris-HCl pH 7.5, as the crude extract. Crude extracts were aliquoted and stored frozen at −80° C. Control extracts were also frozen and used in the same manner. Up to 5 μl aliquots of two-fold serial dilutions of the crude lysates were assayed for cytotoxic activity in the absence of Actinomycin D. Lysate of bacteria transfected with vector alone as negative control.

Example 3

Site-Directed Mutagenesis

Muta-Gene phagemid in vitro mutagenesis kits were obtained from Bio-Rad (Hercules, Calif.) and used according to the directions supplied by the manufacturer. PUC118htnf DNA was transferred into *E. coli* CJ236 [dut, ung, thi, rel A:pCJ105 ($Cm^r$)]. A clone of the transformed CJ236 carrying PUC118htnf was then infected with helper phage VCSM13 to produce phage particles containing uracil substituted single stranded recombinant DNA which was extracted and annealed to mutagenic oligonucleotide. After synthesis of complementary strand and ligation, the covalently closed circular DNA was used to transform MV1190. All mutant clones were screened by DNA sequencing of double stranded phagemid DNA. Three to four clones of transformed MV1190 were picked and double stranded phagemid DNAs were extracted from five ml overnight cultures of each clone and the purified DNAs were subjected to automated DNA sequencing using a Dyedeoxy Cycle Sequencing Kit (Applied Biosystems, Inc. Foster City, Calif.) with an Applied Biosystems Model 373A DNA sequencing system according to the manufacturer's protocol. Oligonucleotides were synthesized on an Applied Biosystems Model 380A DNA synthesizer. Synthetic oligonucleotides used in mutagenesis were all 17-mer with the mis-matched nucleotide at or near the center of the molecule. For each residue selected for mutagenesis, many single amino acid substitution mutants were created by altering one or more bases in the selected codon at a time.

Example 4

Cytotoxicity Assays

Standard in vitro cytotoxicity assays were performed using L929 cells using purified recombinant human TNF-α or crude bacterial lysates containing wild type or mutant TNF proteins. For in vitro cytotoxicity inhibition assay, 2 to 4 units of purified human rhTNF-α was added to media containing 0.5 to 1 μg/ml of Actinomycin D in the presence of serial two fold dilutions of *E. coli* crude lysate containing mutant TNF.

Example 5

Iodination of Recombinant TNF purified recombinant human TNF-α was labeled with $^{125}I$ by the Iodogen method as follows. Iodogen (Pierce, Rockford, Ill.), at a concentration of 5 mg/ml in $CHCl_3$, was used to coat polypropylene tubes. After standing at room temperature for 5 minutes, the tubes were dried under a stream of nitrogen gas. The tubes were then sealed with parafilm and stored in a sealed plastic bag with a drying agent at −20° C. To each tube coated with Iodogen, 1 mCi of $^{125}I$ (as NaI in NaOH from Amersham, Arlington Heights, Ill. or ICN, Costa Mesa, Calif.) in 10 μl was added, followed by 20 μl of 0.5M sodium phosphate buffer (pH 7.4) and 10–20 μg of purified recombinant TNF, freshly dissolved in phosphate buffered saline. After incubating at room temperature for 5 minutes with occasional gentle mixing, the reaction mixture was transferred into a second tube with 55 μl of column buffer containing phosphate buffered saline without $Ca^{2+}$ and $Mg^{2+}$, 1% bovine serum albumin, and 5 μl of 40 mg/ml NaI and passed over a pre-equilibrated Sephadex G25 column. The column was then developed with the same buffer. Fractions of 0.5 ml were collected in 1.5 ml sterilized polypropylene tubes pre-coated with 1% BSA in column buffer. Five μl aliquots of each fraction were counted in a γ counter and the peak fractions were pooled and stored at 4° C. The recovery of TNF following iodination was approximately 60% as determined by SDS Page followed by silver staining of the gel. The specific activity of $^{125}I$-TNF was approximately 200–500 Ci/mmol monomer TNF or 600–1500 Ci/mmol trimeric TNF.

Example 6

Protein Quantification by SDS-PAGE, Silver Staining or Coumassie Blue Staining and Densitometry Measurement Recombinant TNF and TNF mutants in bacterial crude lysates were quantified by fractionation of crude bacterial lysates in a 12% standard Laemmli SDS/PAGE and stained with Coumassie Blue Stain followed by densitometry measurement of the TNF band corresponding to the position of purified recombinant hTNF. Control background was subtracted from the densitometry measurement of a control lane containing crude extract of bacteria infected with PUC118.

Example 7

Protein Quantification by SDS-PAGE and Western Blot Analysis

Bacterial crude lysates, 2–5 μl, were fractionated on a standard Laemmli SDS/PAGE, with control lanes containing crude lysate from vector transfected host and purified recombinant hTNF-α, and the gel stained with Coumassie Blue Stain. The Coumassie Blue stained gels were scanned with an LKB densitometer UltroScan XL (Piscataway, N.J.). To estimate the protein yield of rhTNF-α, in percent of total bacterial protein, peak areas corresponding to rTNF were measured using a peak area integration program, with the control background value subtracted. Control background value was derived from measurement of the control lane containing identical amount of bacterial extract on the same gel. From Western analysis, 7.5 μl of bacterial crude lysates containing TNF or TNF mutants were fractionated on a standard 12% SDS polyacrylamide gel. The proteins in the gel were then transferred onto nitrocellulose membranes in 20–30% methanol, 35 mM Tris-HCl, pH 7.0, 192 mM glycine, by electroblotting at 75 V for 16–22 hours using a Bio-Rad gel blotting apparatus (Hercules, Calif.). The nitrocellulose filters were then blocked with RIPA buffer (3% bovine serum albumin (fraction V), 0.9% NaCl, 20 mM Tris-HCl, pH 7.0, 1 mM EDTA, 0.5% triton X-100) for 1 hour at 37° C. with shaking. After three 15 minute washes at 37° C., the filters were then treated with 1:4000 diluted rabbit antisera to recombinant human TNF in the same buffer for 1 hour at 37° C. followed by three 15 minute washes with RIPA buffer at 37° C. After incubation with $1\times10^7$ cpm of $^{125}I$-protein A in 10 ml RIPA buffer at 37° C. for 30 minutes, followed by three washes with RIPA buffer at 37° C., the filters were exposed to X-ray film for 2 hours or more until the signals are optimal. Recombinant TNF protein yields were estimated from the intensity of the band on the x-ray film, relative to the band intensity of control lanes containing various values of purified rhTNF-α.

Example 8

Receptor Binding Inhibition Assay

The affinity of the mutant TNF proteins for TNFR-p55 and TNFR-p75 was determined in a solid phase radioligand competition binding assay. Ninety-six well microtiter immunoplates were coated overnight at 4° C. with ligand affinity purified recombinant soluble TNFR-p55 and TNFR-p75 (extracellular portion of the receptors, from the amino terminal to the last amino acid before the transmembrane domains of the human TNF receptors, were expressed with a baculovirus expression system using the baculovirus expression kit from Clontech, Palo Alto, Calif., in accordance with manufacturer's directions) at 10 ng/50 μl/well and 25 ng/50 μl/well in phosphate buffered saline (PBS), respectively. After blocking with 1% non-fat dry milk in PBS containing 0.02% $NaN_3$ for 2 hours at 4° C., the plates were washed with the same buffer containing 0.1% non-fat milk and incubated with 1 ng/100 μl of $^{125}I$-TNF-α in the same solution and with various dilutions of *E. coli* crude lysate or purified mutant TNF proteins. Control experiments contained 200 fold excess of cold hTNF-α. Binding reactions were performed at room temperature for 4 hours. After the wells were washed 4 times with PBS, individual wells were separated, transferred into counting vials and counted in the γ counter. The ratio of the amount of mutant TNF required to inhibit half of the $^{125}I$-type TNF ($ID_{50}$ mutant)

over the corresponding amount of wild type TNF ($ID_{50}$ wt) was calculated to determine a percent wild type binding capacity of each mutant protein, i.e. % wt binding capacity of a mutant=($ID_{50}$ wt/$ID_{50}$ mutant)×100. Results from binding experiments are shown in Table 1.

TABLE 1

Summary of in vitro binding experiments

| MUTANT | TNFR-p55 Binding | TNFR-p75 Binding | Ratio (TNFR-p75/ TNFR-p55) |
|---|---|---|---|
| Wild type | 100% | 100% | 1 |
| A33-Asn | 10% | 109% | 11 |
| A33-Gln | 13% | 14% | 1.1 |
| A33-Ile | 3% | 101% | 34 |
| A33-Val | 0.6% | 44% | 73 |
| A33-Met | 67% | 119% | 1.8 |
| A33-Lel | 17% | 105% | 6 |

In this assay, all mutant proteins, with the exception of A33-Ile, were partially purified through one step cation exchanger chromatography (SP-Sepharose, LKB Biotechnology, Piscataway, N.J.) before receptor binding inhibition assays were performed. Wild type and A33-Ile mutants were purified to homogeneity through two steps ion exchange chromatography (SP-Sepharose followed by Q-Sepharose, LKB Biotechnology, Piscataway, N.J.). These results indicate that mutation of the alanine at position 33 to isoleucine, valine, asparagine or leucine were most effective in altering binding affinity to TNFR-p55 while maintaining binding affinity for TNFR-p75 at full or near full capacity.

Figure 1B:
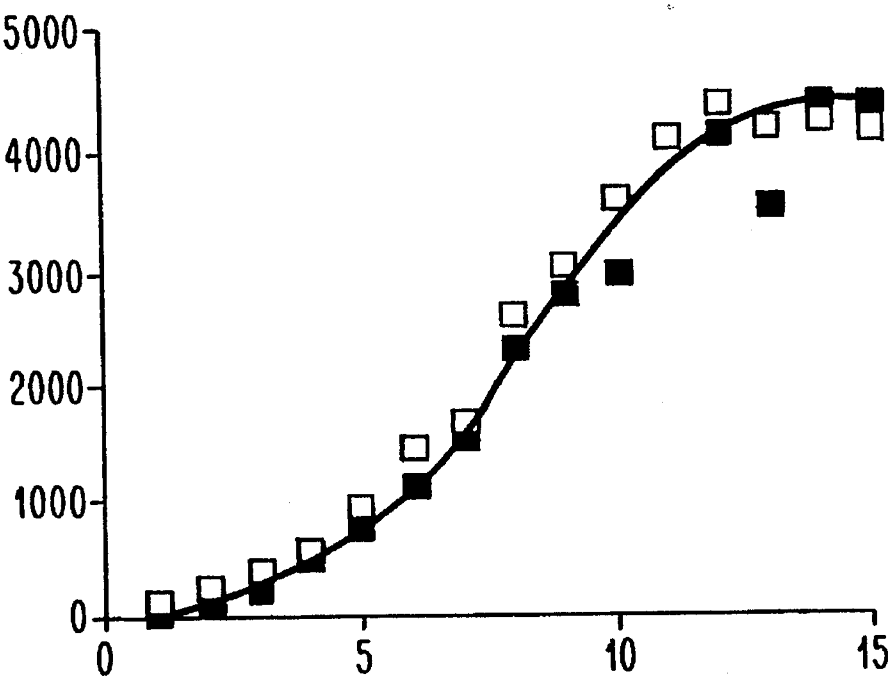

Binding inhibition assays using purified mutant TNF protein A33-Ile and wild type TNF were also performed using a very similar assay. The results of these experiments are shown in FIG. 1. In these assays, 2 ng/100 μl TNFR-p55 in PBS (FIG. 1A) and 10 ng/100 μl TNFR-p75 in PBS (FIG. 1B) proteins were used to coat the wells of a 96-well microtiter plate. The plates were incubated overnight and washed and blocked as described above. One to two ng of 125I-TNF (about 400 Ci/mmole and a total of approximately $1\times10^5$ cpm) were added, in duplicate, in the presence of 256 ng (dilution 1) of wild type or equivalent $A_{280}$ units of mutant TNF (I $A_{280}$–0.5 mg TNF, wt, 0.47 mg/ml of A33-Ile) followed by two-fold dilutions down to 0.156 ng/well. After binding at room temperature for 4 hours, the wells were washed 4 times with PBS containing 0.1% BSA and counted as previously described. Wild type TNF and the mutant TNF protein A33-Ile showed similar binding affinity for the TNFR-p75 receptor (FIG. 1B), however, the mutant protein showed a much decreased affinity for the TNFR-p55 receptor (FIG. 1A).

What is claimed is:

1. A mutant human tumor necrosis factor protein wherein human tumor necrosis factor is mutated at position 33 by substitution with isoleucine, leucine, asparagine or valine.

2. A pharmaceutical composition comprising a mutant human tumor necrosis factor protein wherein human tumor necrosis factor is mutated at position 33 by substitution with isoleucine, leucine, asparagine or valine, in a pharmaceutically effective carrier, vehicle or auxiliary agent.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 59
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO:1:

CTAAGGAAAT ACTTACATAT GGTACGTTCT TCTTCTCGTA CTCCGAGTGA 50

CAAGCCTGT 59

( 2 ) INFORMATION FOR SEQ ID NO:2:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: No ( x i ) SEQUENCE DESCRIPTION: SEQ ID NO:2:

TTAAAGTTCT AAGCTTGGGT 20

( 2 ) INFORMATION FOR SEQ ID NO:3:

( i ) SEQUENCE CHARACTERISTICS:
( A ) LENGTH: 61
( B ) TYPE: Nucleic Acid
( C ) STRANDEDNESS: Single
( D ) TOPOLOGY: Linear -continued ( i v ) ANTI-SENSE: No ( x i ) SEQUENCE DESCRIPTION: SEQ ID NO:3:

```
TCGACATGCA TTTATTTGCA TACATTCAAT CAATTGTTAT CTAAGGAAAT    50

ACTTACATAT G                                              61
```